US00PP16402P3

(12) United States Plant Patent

Olesen et al.

(10) Patent No.: US PP16,402 P3
(45) Date of Patent: Apr. 4, 2006

(54) HYBRID TEA ROSE PLANT NAMED 'POULHT002'

(50) Latin Name: *Rosa hybrida*
Varietal Denomination: POULht002

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 136 days.

(21) Appl. No.: 10/813,546

(22) Filed: Mar. 29, 2004

(65) Prior Publication Data

US 2005/0172372 P1 Aug. 4, 2005

(51) Int. Cl.
*A01H 5/00* (2006.01)

(52) U.S. Cl. ..... Plt./132

(58) Field of Classification Search ..... Plt./130, Plt./131, 132, 134, 137, 138, 133, 141, 143
See application file for complete search history.

*Primary Examiner*—Howard J. Locker

(57) ABSTRACT

A new garden rose plant of the hybrid tea class which has abundant, apricot flowers and attractive foliage. This new and distinct variety has shown to be uniform and stable in the resulting generations from asexual propagation.

2 Drawing Sheets

Botanical classification: *Rosa hybrida.*
Variety denomination: 'POULht002'.

SUMMARY OF THE INVENTION

The present invention constitutes a new and distinct variety of garden rose plant which originated from a controlled crossing between the female seed parent 'POULduce', originally described and illustrated in U.S. Plant patent application Ser. No. 09/277,239 dated March 26, now abandoned, and the male pollen parent, an un-named seedling. The two parents were crossed during the summer of 1993 and the resulting seeds were planted in a controlled environment in Fredensborg, Denmark. The new variety is named 'POULht002'.

The new variety may be distinguished from its seed parent, 'POULduce' by the following combination of characteristics:

1. While flowers of the seed parent have a general tonality of Yellow Group 3C–4D, flowers of 'POULht002' have a general tonality of White Group 155A with intonations of Yellow Group 5A and Red Group 53B to 53C.
2. While the seed parent 'POULduce' has a flower petal count of 50–65 petals, 'POULht002' has 40 petals.

The new variety may be distinguished from its pollen parent by the following combination of characteristics:

1. While the pollen parent has strong pink and orange flowers, flowers of 'POULht002' are a blend of apricot and other light pink hues.
2. 'POULht002' is more disease resistant than the pollen parent.

The objective of the hybridization of this rose variety was to create a new and distinct variety for garden use with unique qualities, such as:

1. Uniform and abundant apricot pink blended flowers;
2. Vigorous, growth;
3. Disease resistance;
4. Exceptional rose fragrance.

This combination of qualities is not present in previously available commercial cultivars of this type, known to the inventors, and distinguish 'POULht002' from all other varieties of which we are aware.

As part of their rose development program, L. Pernille Olesen and Mogens N. Olesen germinated the seeds from the aforementioned hybridization during winter of 1993 and conducted evaluations on the resulting seedlings in a controlled environment in Fredensborg, Denmark.

'POULht002' was selected in the spring 1994 by the inventors as a single plant from the progeny of the aforementioned hybridization.

Asexual reproduction of 'POULht002' by traditional budding and rooted cuttings was first done by L. Pernille and Mogens N. Olesen in their nursery in Fredensborg, Denmark in July, 1994. This initial and other subsequent asexual propagations conducted in controlled environments have demonstrated that the characteristics of 'POULht002' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULht002'.

Specifically illustrated in FIG. 1:

FIG. 1.1; Open flower, stem showing open flower, and the attachment of leaves and peduncles;

FIG. 1.2; Flower bud as sepals unfold, and partially open;

Specifically illustrated in FIG. 2:

FIG. 2.1; Flower petals, detached;

FIG. 2.2; Sepals, receptacle, and peduncle;

FIG. 2.3; Juvenile leaves;

FIG. 2.4; Mature leaf;

FIG. 2.5; Juvenile growth exhibiting anthocyanin;

FIG. 2.6; Section of bare stem exhibiting thorns.

DETAILED DESCRIPTION OF THE VARIETY

The following is a description of 'POULht002', as observed in its growth in a field nursery in Jackson County, Oreg. Observed plants are 3 years of age and were grown as *Rosa multiflora* understock. Color references are made using The Royal Horticultural Society (London, England) Colour Chart, 1995, except where common terms of color are used.

For a comparison, several physical characteristics of the most similar rose variety we are aware of, 'Hombre', described and illustrated in U.S. Plant Pat. No. 5,552 issued Sep.10, 1985, are compared to 'POULht002' in Chart 1.

CHART 1

| | 'POULht002' | 'Hombre' |
|---|---|---|
| Petal color as sepals first divide | Yellow-Orange Group 22B with intonations of Red Group 47A | Orange Group 25D |
| General tonality | On open flower White Group 155A with intonations of Yellow Group 5A and Red Group 53B to 53C | Hues vary. White or near white with a pinkish cast, approaching 36D, to near white with slight orange cast, approaching 27D |
| Thorn color | Greyed-Red Group 181A | Near Yellow-Green Group 144B |

FLOWER AND FLOWER BUD

Blooming habit: Continuous.

Flower bud:

*Size.*—Upon opening, 33 mm in length from base of receptacle to end of bud. Bud diameter is 23 mm.

*Bud form.*—Broad-based pointed ovoid.

*Bud color.*—As sepals unfold, petals are Yellow-Orange Group 22B with intonations of Red Group 47A.

*Sepals.*—Upper Surface: Color: Yellow-Green Group 144B. Surface: Moderately pubescent with stipitate glands present in medium quantity. Lower Surface: Color: Yellow-Green Group 144B. Anthocyanic pigments the color of Greyed-Purple Group 183A observed. Sepal Shape: Sepal apex is cirrhose. Base is flat at union with receptacle. Sepal Margin: Margins have weak foliaceous appendages on three of the five sepals. Size: 35 mm (l)×14 mm (w).

*Receptacle.*—Surface: Smooth and glabrous. Shape: Funnel to urn-shaped. Size: 9 mm (h)×11 mm (w). Color: Yellow-Green Group 144A. Anthocyanic pigments the color of Greyed-Purple Group 183A observed.

*Peduncle.*—Surface: Smooth and glabrous. Length: 50 to 60 mm. Width: 4 mm. Color: Yellow-Green Group 144A. Anthocyanic pigments the color of Greyed-Purple Group 183A. Strength: Strong.

*Borne.*—Singularly.

Flower bloom:

*Fragrance.*—Moderate to strong rose scent.

*Duration.*—The blooms have a duration on the plant of approximately 10 to 14 days. Petals fall cleanly away from plant after flowers fully mature.

*Size.*—Flower diameter is 130 mm when open. Flower depth is 50 mm.

*Form.*—Flowers are initially high centered with petals tightly closed. As flowers mature, the petals reflex outward.

*Shape of flower when viewed from the side.*—Upon opening, upper part: Flat. Upon opening, lower part: Flattened Convex. Open flower, upper part: Flattened Convex. Open flower, lower part: Deeply Concave.

Petalage: On average 40 petals under normal conditions with 9 petaloids.

Color:

Upon opening, petals:

*Outermost petals.*—Outer side: White Group 155B at marginal zone with light intonations of Red-Purple Group 53A at petal edges, Yellow Group 5D at middle zone and Yellow Group 5C at basal zone. Inner Side: Yellow-Orange Group 19D with intonations of Red Group 53B at petal margins and Yellow Group 5D at petal margins and basal zone.

*Innermost petals.*—Outer side: White Group 155B at marginal zone with light intonations of Red-Purple Group 53A at petal edges, Yellow Group 5D at middle zone and Yellow Group 5C at basal zone. Inner Side: Yellow-Orange Group 19D with intonations of Red Group 53B at petal margins and Yellow Group 5D at petal margins and basal zone.

Upon opening, basal petal spots:

*Outermost petals.*—Outer side: None. Inner Side: Yellow Group 5A.

*Innermost petals.*—Outer side: None. Inner Side: Yellow Group 5A.

After opening, petals:

*Outermost petals.*—Outer side: White Group 155B at marginal zone with light intonations of Red-Purple Group 53A at petal edges, Yellow Group 5D at middle zone and Yellow Group 5C at basal zone. Inner Side: Yellow-Orange Group 19D with intonations of Red Group 53B at petal margins and Yellow Group 5D at petal margins and basal zone.

*Innermost petals.*—Outer side: White Group 155B at marginal zone with light intonations of Red-Purple Group 53A at petal edges, Yellow Group 5D at middle zone and Yellow Group 5C at basal zone. Inner Side: Yellow-Orange Group 19D with intonations of Red Group 53B at petal margins and Yellow Group 5D at petal margins and basal zone.

After opening, basal petal spots:

*Outermost petals.*—Outer side: None. Inner Side: Yellow Group 5A.

*Innermost petals.*—Outer side: None. Inner Side: Yellow Group 5A.

General tonality: On open flower White Group 155A with intonations of Yellow Group 5A and Red Group 53B to 53C. No change in the general tonality at the end of the $10^{th}$ day.

Petals:

*Petal reflex.*—Somewhat reflexed.

*Margin.*—Entire and uniform. Medium undulations of margin observed.

*Shape.*—Apex: Round. Base: Acute.

*Size.*—66 mm (l)×65 mm (w).

*Texture.*—Smooth.

*Thickness.*—Thick.

*Arrangement.*—Not Formal.

Petaloids:

*Quantity.*—8 to 15.

*Color.*—Yellow Group 5D.

*Shape.*—Apex is rounded. Base is acute.

*Size.*—55 mm (l)×23 mm (w).

Reproductive organs:

*Pistils.*—Length: 9 mm. Quantity: 100 (actual count).

*Anthers.*—Size: 2 mm long. Color: Yellow-Orange Group 17A. Quantity: 100 (actual count). Pollen: None observed.

*Filaments.*—Color: Yellow-Orange Group 17A. Length: 5 mm.

*Stigmas.*—Superior in location to the height of the anthers. Color: Yellow-Green Group 154D.

*Styles.*—Color: Yellow-Green Group 154D.

*Hips.*—None Observed in the field nursery in Jackson County, Oreg.

PLANT

Plant growth: Moderate, upright to bushy. When grown as a budded field grown plant on *Rosa multiflora* understock, the average height of the plant is 60 to 75 cm and the average width is 60 cm.

Stems:

*Color.*—Young wood: Yellow-Green Group 144A. Anthocyanin: Greyed-Red Group 181A in new shoots. Older wood: Yellow-Green Group 144A.

*Surface texture.*—Young wood: Smooth. Older wood: Smooth.

Thorns:

*Incidence.*—12 thorns per 10 cm of stem.

*Size.*—Average length: 8 mm.

*Color.*—Greyed-Red Group 181A.

*Shape.*—Deeply concave.

Plant foliage: Normal number of leaflets on normal leaves in middle of the stem: 5 leaflets.

*Command leaf size.*—195 mm (l)×130 mm (w).

*Color.*—Mature Foliage: Upper surface: Yellow-Green Group 147A. Lower surface: Yellow-Green Group 146C. Juvenile foliage: Upper surface: Greyed-Purple Group 187A. Lower surface: Greyed-Purple Group 187A. Anthocyanin: Location: New shoots and leaves. Color: Greyed-Purple Group 187A to Greyed-Purple Group 183A.

Plant leaves and leaflets:

*Stipules.*—Size: 30 mm in length. Shape: Linear with outward extending apices. Quantity: 2 per compound leaf. Margins: Finely serrated with abundant stipitate glands. Color: Yellow-Green Group 144A. Anthocyanin: Color: Greyed-Red Group 181A.

*Petiole.*—Length: 45 mm. Color: Yellow-Green Group 144B. Anthocyanin: Greyed-Red Group 181C. Underneath: A few stipitate glands and thorns observed.

*Rachis.*—Length: 55 mm. Above: Color: Yellow-Green Group 144B. Anthocyanin: Color: Greyed-Orange Group 166A. Underneath: A few stipitate glands and thorns observed.

*Leaflet.*—Edge: Finely serrated. Size: 70 mm (l) by 40 mm (w). Shape: Generally ovate. Base is round. Apex is cuspidate. Texture: Smooth. Thickness: Thick. Arrangement: Odd pinnate. Venation: Reticulate. Glossiness: Very glossy.

Disease resistance: Above average resistance to mildew, rust, black spot, and *Botrytis* under normal growing conditions in Jackson County, Oreg.

Cold hardiness: The variety 'POULht002' has been found to be cold tolerant to USDA Cold Hardiness Zone 6.

It is claimed:

1. A new and distinct variety of rose plant of the hybrid tea rose class named 'POULht002', substantially as herein illustrated and described as a distinct and novel rose variety due to its abundant apricot and pink blended flowers, disease resistance, and extended period of bloom.

* * * * *

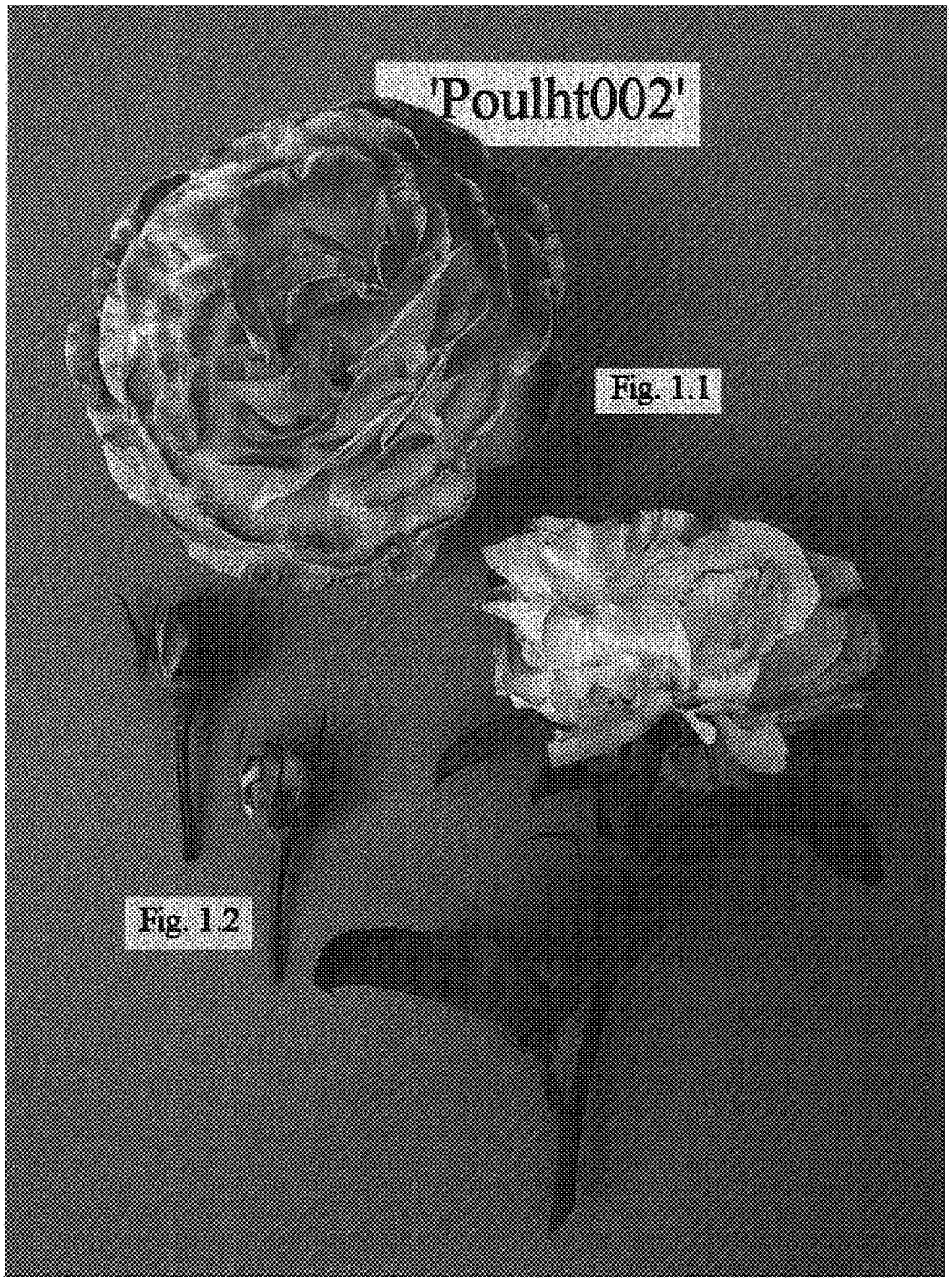
'Poulht002'
Fig. 1.1
Fig. 1.2

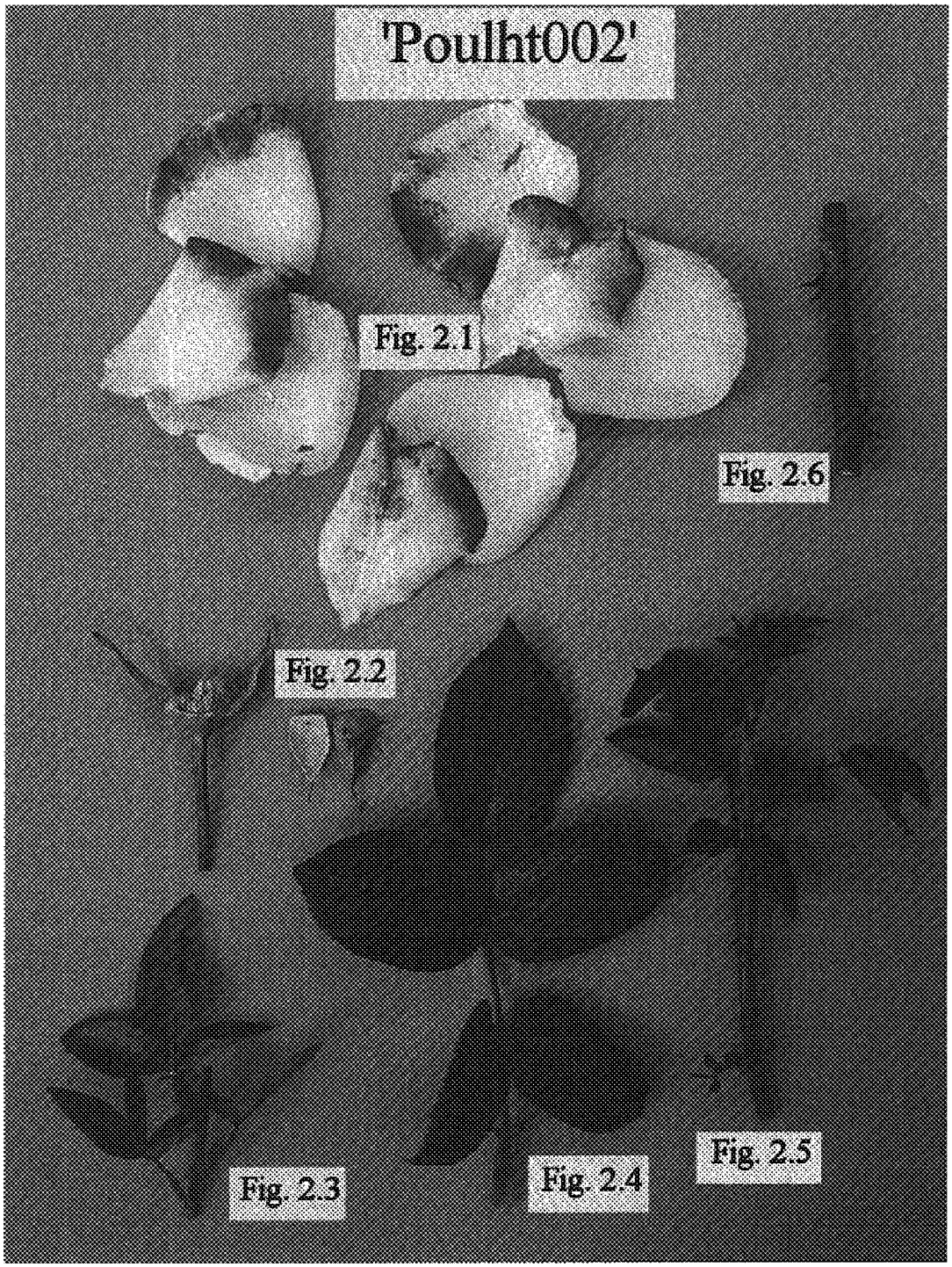
'Poulht002'
Fig. 2.1
Fig. 2.2
Fig. 2.3
Fig. 2.4
Fig. 2.5
Fig. 2.6